United States Patent
Rehkemper et al.

(10) Patent No.: US 6,689,078 B1
(45) Date of Patent: Feb. 10, 2004

(54) SELF-CONTAINED ORAL CLEANING DEVICE

(75) Inventors: Steven Rehkemper, Chicago, IL (US); Jeffrey Rehkemper, Chicago, IL (US); Peter Greenley, Chicago, IL (US)

(73) Assignee: Rehco, LLC, Chicago, IL (US)

( * ) Notice: Subject to any disclaimer, the term of this patent is extended or adjusted under 35 U.S.C. 154(b) by 0 days.

(21) Appl. No.: 10/315,730

(22) Filed: Dec. 10, 2002

Related U.S. Application Data (63) Continuation-in-part of application No. 10/233,687, filed on Sep. 4, 2002.

(51) Int. Cl.[7] .......................... A61G 17/02; A61H 9/00
(52) U.S. Cl. ............................. 601/162; 433/80; 15/29
(58) Field of Search .......................... 601/88, 96, 105, 601/139, 154, 155, 160–163, 165, 166; 433/80, 81, 84, 88, 89, 95, 114, 131, 175; 15/22.1, 24, 29; 401/175, 209, 279

(56) References Cited

U.S. PATENT DOCUMENTS

| | | | |
|---|---|---|---|
| 3,144,867 A | | 8/1964 | Trupp et al. |
| 4,146,020 A | | 3/1979 | Moret et al. |
| 4,181,997 A | | 1/1980 | O'Rourke |
| 4,257,433 A | | 3/1981 | Kwan |
| 4,412,823 A | | 11/1983 | Sakai et al. |
| 4,660,244 A | | 4/1987 | Polyak |
| 4,958,629 A | | 9/1990 | Peace et al. |
| 4,979,503 A | | 12/1990 | Chernack |
| 5,033,961 A | * | 7/1991 | Kandler et al. ............... 433/89 |
| 5,142,723 A | | 9/1992 | Lustig et al. |
| 5,197,460 A | * | 3/1993 | Ito et al. ..................... 601/162 |
| 5,252,064 A | * | 10/1993 | Baum et al. .................. 433/80 |
| 5,304,010 A | | 4/1994 | Hsing-San |
| 5,321,865 A | * | 6/1994 | Kaeser ....................... 15/22.1 |
| 5,500,973 A | | 3/1996 | Phelan |
| 5,640,735 A | | 6/1997 | Manning |
| 5,683,192 A | | 11/1997 | Kilfoil |
| 6,030,215 A | | 2/2000 | Ellion et al. |
| 6,047,429 A | | 4/2000 | Wu |
| 6,129,547 A | * | 10/2000 | Cise et al. .................... 433/80 |
| 6,164,967 A | * | 12/2000 | Sale et al. .................... 433/80 |
| 6,331,088 B2 | | 12/2001 | Owens |

FOREIGN PATENT DOCUMENTS

| | | |
|---|---|---|
| JP | 09322823 | 12/1997 |
| WO | WO 00/41645 | 7/2000 |

* cited by examiner

*Primary Examiner*—Nicholas D. Lucchesi
*Assistant Examiner*—Quang D Thanh (57) ABSTRACT

In accordance with one embodiment of the present invention, an oral cleaning device is provided with a nozzle to jet a pressurized liquid. The oral cleaning device has a body, a neck extending from the body and a head attached to the neck. The oral cleaning device further includes a refillable reservoir defined by the body for holding a liquid. An on-board pump is used to pressurize the liquid contained in the reservoir. The oral cleaning device further includes a channel from the reservoir to the nozzle in the head such that when pressurized fluid in the reservoir is released, the fluid jets from the oral cleaning device. The head and neck assembly is also interchangeable with other head and neck assemblies to provide different cleaning features. First, the nozzle by itself to remove plaque and to simulate flossing between teeth. Second, the nozzle with bristles and the head shaped to brush teeth. Third, the nozzle with bristles and the head shaped to brush a tongue. Finally, a head defined to scrape a tongue.

33 Claims, 4 Drawing Sheets

SELF-CONTAINED ORAL CLEANING DEVICE

CROSS REFERENCE TO RELATED APPLICATIONS

The present invention is a continuation in part of U.S. application Ser. No. 10/233,687, filed Sep. 4, 2002, and entitled "Pneumatic-Operated Toothbrushes".

FIELD OF THE INVENTION

The present invention relates to oral cleaning devices such as toothbrushes and water jets and in particular to a self-contained oral cleaning device with a liquid jet feature.

BACKGROUND OF THE INVENTION

Oral cleaning devices that employ a water jet feature are known in the art and such devices use an external supply of water. In one category of the prior art, a toothbrush is tethered or connected to a faucet. The water pressure from the faucet is used to propel the water through the toothbrush and out the head of the toothbrush and/or used to power a motor that is used to rotate or move bristles. For example, U.S. Pat. No. 5,304,010 discloses a toothbrush that includes a hollow body, an opening by the head of the toothbrush, and a water inlet that is tethered and attached to a faucet. In another example, U.S. Pat. No. 4,181,997 discloses a toothbrush that is also tethered to a faucet. However, the toothbrush uses the water pressure to power an impeller to move bristles on the head of the toothbrush. In both patents, the water is already pressurized and flowing; the water also cannot be stagnant because the toothbrush does not include any mechanism, on its own, to propel the water out of the toothbrush. Additional toothbrushes that are tethered to a faucet or external source of running water may be found in U.S. Pat. No. 5,863,192, discloses a toothbrush tethered to a shower head; U.S. Pat. Nos. 5,500,973 and 4,257,433, disclose toothbrushes tethered to faucets; and U.S. Pat. No. 4,412,823, discloses a toothbrush tethered to an external source of water that is pumped into and through the toothbrush.

In another category of prior art, electric toothbrushes are connected to an external reservoir of water. For example, U.S. Pat. No. 6,047,429 combines a mechanical toothbrush with a water jet feature. The motor used to move the bristles is also used to draw water from an outside source, not contained within the toothbrush. The water is drawn from the outside source, propelled through the neck of the toothbrush, and expelled out of the head of the toothbrush. Other electric toothbrushes which are tethered to a source of water include U.S. Pat. Nos. 4,958,629 and D318,918.

Various problems in both categories exist and are associated with the fact that the toothbrush must be tethered or connected to an outside source of water. In the first instance, when the toothbrush is tethered to a faucet, the user cannot use the toothbrush to spray other liquids such as antiseptic solutions. In the second instance, when the toothbrush is connected to an outside reservoir of water, the user's range of motion is limited as the end of the tether must remain in the outside reservoir at all times. In addition, when an electric toothbrush is tethered to an outside source, the user cannot control the force in which the water is propelled out of the toothbrush. The force is pre-set by the speed of the motor and can only be turned on or off. Furthermore, the units are bulky and are not made to be portable, oftentimes causing the user to own a separate toothbrush for traveling.

With the onset of mechanical and electrical toothbrushes the total cost of the oral cleaning devices have increased. To offset the overall price of the devices the heads of the toothbrushes have been made replaceable. As such, after the bristles become worn from continual use, the head may be replaced without replacing the whole unit. However, the worn heads are simply replaced with an identical head to provide the same type of cleaning. The ability to interchange heads to provide different types of cleaning, for example to interchange heads to provide a water jet for removing plaque, to provide a brush with water jet for cleaning teeth and gums, and to provide a brush or scraper with water jet for cleaning the tongue, is not widely incorporated with prior art oral cleaning devices.

It is therefore an object of the present invention to provide a self-contained, total oral cleaning device that incorporates a nozzle for jetting a pressurized fluid into a user's mouth. The oral cleaning device in accordance with the present invention includes a reservoir for holding a liquid and a pump for pressurizing the liquid contained in the reservoir. The reservoir is contained within the oral cleaning device eliminating the need to tether the device to a faucet or attach the device to an outside source of liquid. The oral cleaning device also includes a means for releasing the pressurized liquid contained within the reservoir out of the oral cleaning device. The oral cleaning device is completely portable and assists the user in cleaning their entire mouth, including the tongue, gums, and teeth, by providing interchangeable heads. The present invention also provides the ability to change the force of the liquid jetting out of the oral cleaning device. Since the user must both fill the reservoir with a liquid and pressurize the liquid by pumping air into the reservoir, the user can change the force of the liquid jetting out of the reservoir by changing either the amount of air pumped into the reservoir or the initial amount of water. In addition a maximum pressurization will be predetermined by setting a pressure-release valve in the device as well as marking a optimum fill-line on the reservoir.

SUMMARY OF THE INVENTION

In accordance with one embodiment of the present invention, a handheld portable self-contained oral cleaning device is provided that includes a refillable reservoir, which a user may be able to partially fill with a liquid up to a predetermined desired level. The reservoir, which acts as a modular handle, includes an on-board pump that a user uses to pressurize the liquid contained in the reservoir. In addition, the number of pumps a user pumps air into the reservoir determines the force of the liquid expelling (explained in greater detail below). The pressurized liquid may then be sprayed out of the oral cleaning device to assist in cleaning the user's mouth. Various interchangeable heads are incorporated herewith to provide the user with a total cleaning experience. First, a head with a nozzle that provides the user with a high-pressure jet of liquid to remove plaque and simulate flossing between teeth and gums. Second, various shaped heads with bristles and a nozzle to provide the user with different brushes to clean teeth and their tongue as well as a jet of liquid that may be turned on to assist in cleaning gums or freshening breath. Lastly, a tongue scraper head with a nozzle, which also assists the user in cleaning their tongue and provides a jet to spray liquid such as water or antiseptic directly onto their tongue while they are scraping.

Numerous other advantages and features of the invention will become readily apparent from the following detailed description of the invention and the embodiments thereof, from the claims, and from the accompanying drawings.

BRIEF DESCRIPTION OF THE DRAWINGS

A fuller understanding of the foregoing may be had by reference to the accompanying drawings, wherein.

DETAILED DESCRIPTION OF THE EMBODIMENTS

While the invention is susceptible to embodiments in many different forms, there are shown in the drawings and will be described herein, in detail, the preferred embodiments of the present invention. It should be understood, however, that the present disclosure is to be considered an exemplification of the principles of the invention and is not intended to limit the spirit or scope of the invention and/or claims of the embodiments illustrated.

Figure 1:
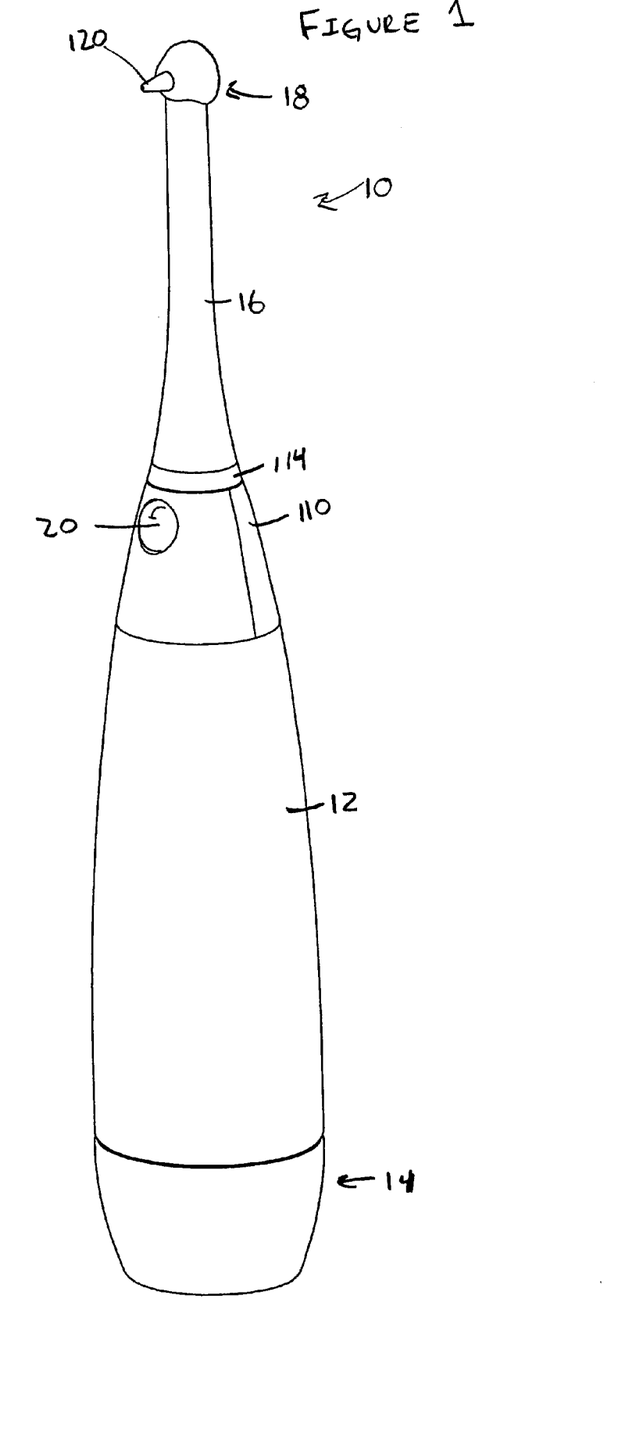
FIG. 1 is a front view of an oral cleaning device having a refillable reservoir that is capable of storing a liquid and having an on-board pump that is used to pressurize the liquid in the reservoir, wherein the pressurized liquid may jet from a nozzle in the head of the device to provide a user with a self-contained device that has a high pressure jet of liquid.

Referring now to FIG. 1, there is disclosed in accordance with the present invention an oral cleaning device generally referenced to as numeral 10. The oral cleaning device includes a body 12 (or handle) that may be gripped by a user. As will be described in detail below, the body 12 is further defined as a refillable reservoir that a user may partially fill with a fluid, for example, the fluid may include a gas, such as air, or a liquid, such as water or an antiseptic solution used for cleaning a user's mouth and freshening breath. The oral cleaning device also includes a means for pressurizing the fluid in the reservoir. The pressurizing means is preferably an on-board pump 14. Once the fluid is pressurized, the fluid in the reservoir may be released by depressing a button 20. The button 20 (illustrated in FIGS. 2 and 3) opens a valve mechanism which controls the flow of the pressurized fluid out of the reservoir. The fluid once released travels through a neck 16 that extends outwardly from the body 12 to a head 18. This neck/head assembly may be interchangeable with other neck/head assemblies to provide the user with different cleaning implements. Alternatively, the neck/head assembly may also be fixed onto the body 12, to provide a single cleaning implement.

Figure 2:
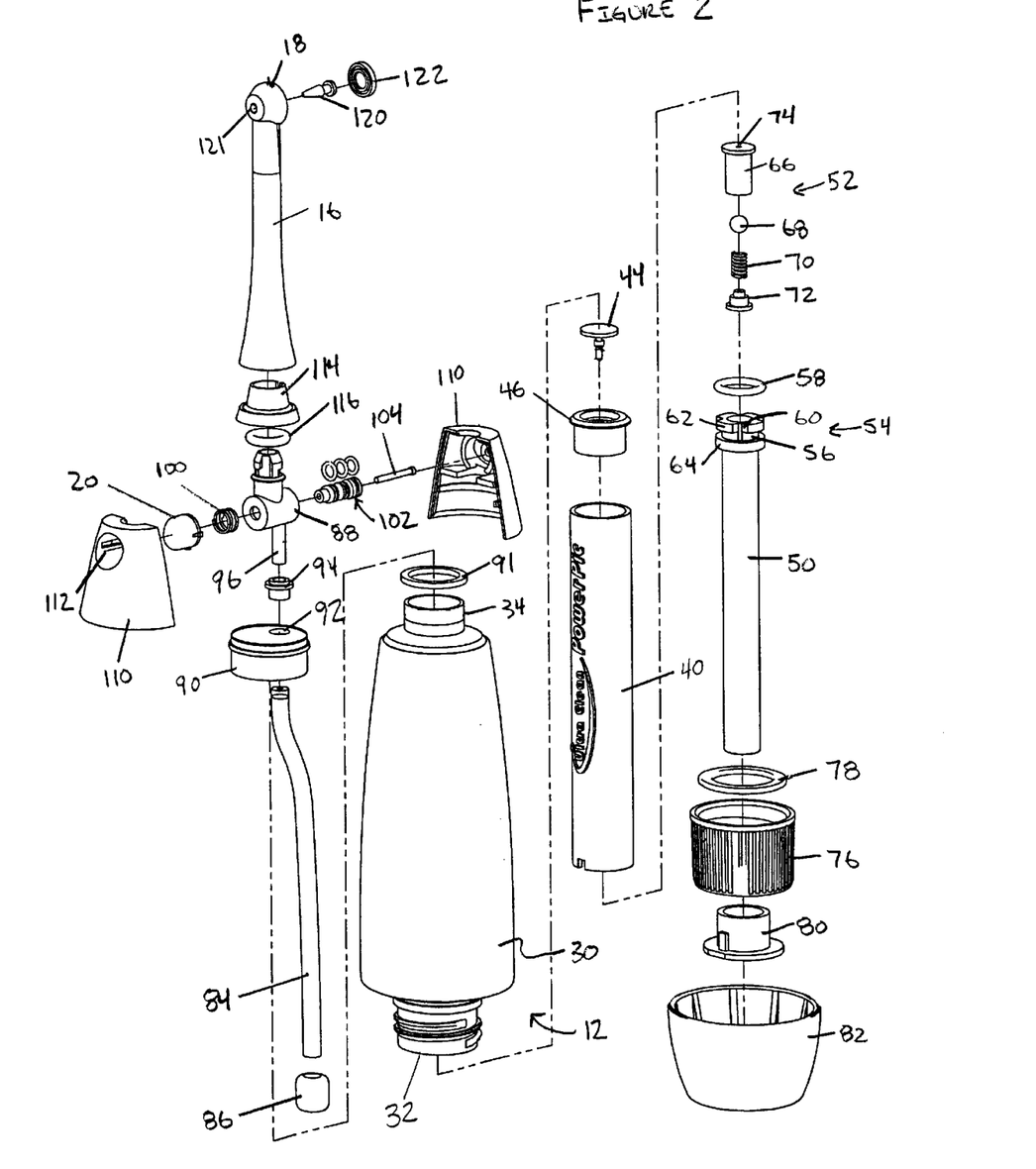
FIG. 2 is an exploded view of the cleaning device of FIG. 1.
Figure 3:
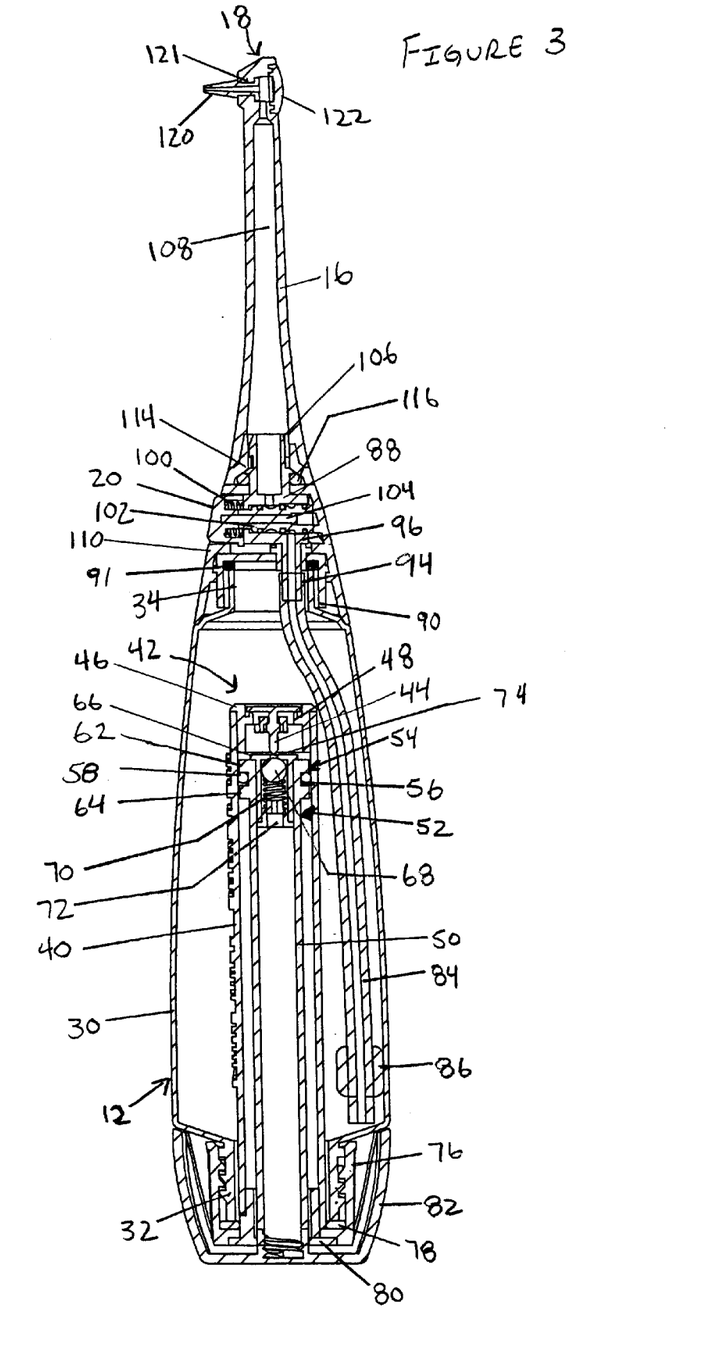
FIG. 3 is a cross-sectional view of the toothbrush of FIG. 1.

Referring now to FIGS. 2 and 3, the oral cleaning device 10 includes a refillable reservoir 30 that also serves as a main portion of the body 12 or handle which the user grips when using the oral cleaning device 10. The refillable reservoir 30 is attached at one end (bottom aperture 32) to an on-board pump 14 and attached at the other end (top aperture 34) to the neck 16. Preferably, the on-board pump 14 is attached to the bottom aperture 32 such that the on-board pump 14 may be easily removed and reattached. This permits the user to pour a liquid (or other fluid) into the reservoir 30 via the bottom aperture 32. However, it is also easy to implement alternative means to refill the reservoir such as but not limited to having a separate resealable inlet. In this instance, the on-board pump 14 would not have to be removable and could be permanently attached thereto.

The on-board pump 14 includes a pump cylinder 40 that slides into the reservoir 30 through the bottom aperture 32 (best seen in FIG. 3). Secured to one end of the pump cylinder 40 is a one-way valve cap 42. The one-way valve cap 42 allows air to be pumped into the reservoir 30, which permits the user to pressurize the liquid (or fluid) inside the reservoir 30. The one-way valve cap 42 also prevents any liquid (or fluid) inside the reservoir 30 from entering the pump cylinder 40. The one-way valve cap 42 includes a flexible valve seal 44 and a valve cap 46. The valve cap 46 attaches to the end of the pump cylinder 40 and includes openings 48 to permit air to travel through. The flexible valve seal 44 is then attached to the valve cap 46 such that the flexible valve seal 44 covers the openings 48 in the valve cap 46. When the user is pumping air through the pump cylinder 40, to pressurize the reservoir 30, air in the valve cap 46 travels through the openings 48 pushing and bending the flexible valve seal 44 away from the openings 48, allowing air to enter into the reservoir 30. This also occurs when the pressure inside the reservoir 30 is lower than a maximum pressure pre-defined by a pressure release valve 52 (discussed in greater detail below). As soon as the user stops pumping air through the pump cylinder 40, the pressure in the reservoir 30 pushes against the flexible valve seal 44 and seals the openings 48, preventing liquid in the reservoir 30 from escaping via the one-way valve cap 42.

Inserted into the pump cylinder 40 is a pump piston 50 that includes the pressure release valve 52. The top 54 of the pump piston 50 has a groove 56, which receives a seal 58. The top 54 also has notches 60 (FIG. 2) running perpendicular to the groove 56. While the pump piston 50 is being pulled away from the pump cylinder 40, the seal 58 moves against the top portion 62 of the groove 56, allowing air to enter the pump cylinder 40, above the top 54 of the pump piston 50, via the notches 60. Subsequently, when pushed into the pump cylinder 40, the seal 58 moves against the bottom portion 64 of the groove 56, preventing air from escaping the pump cylinder 40. As such, when the pump piston 50 is pushed into the pump cylinder 40, air inside the pump cylinder 40, above the top 54 of the pump piston, will be forced into the reservoir 30, again as long as the pressure inside the reservoir 30 is lower than the maximum pressure provided for on the pressure release valve 52.

When the pressure inside the reservoir 30 is greater than the maximum pressure provided for by the pressure release valve 52, the air inside the pump cylinder 40 above the top 54 of the pump piston 50 will vent through the pressure release valve 52. The pressure release valve 52 includes a release housing 66, a release ball 68, a release spring 70, and a release cap 72. The release ball 68 is held by the release spring 70 against a release aperture 74 defined in the release housing 66. When the pressure in the reservoir 30 is greater than the pressure exerted by the release spring 70 on the release ball 68, the air will push against the release ball 68 compressing the release spring 70 permitting the air to vent through the release aperture 74 and into the pump piston 50. Eventually the air will vent out of the device 10 through an aperture (not shown) on the pump handle 82.

The reservoir 30, pump cylinder 40, and pump piston 50 are secured and captured by various end caps that secure them separately to the device 10. The reservoir 30 is removably attached to a reservoir cap 76, which may be removed when filling the reservoir 30 with a liquid. A reservoir gasket 78 is positioned between the reservoir 30 and reservoir cap 76 to prevent liquid (or fluid) inside the reservoir 30 from leaking. The pump cylinder 40 extends through the reservoir gasket 78 and reservoir cap 76 and is secured to a pump cylinder cap 80. Extending through the pump cylinder cap 80 is the pump piston 50, which is attached to a pump handle 82. The user is also prevented from pulling the pump piston 50 entirely out of the pump cylinder 40 because the top 54 of the pump piston 50 is larger than an opening defined in the pump cylinder cap 80.

Since the operation of the on-board pump 14 has already been partially explained, it can be further stated that when in operation a user can remove the on-board pump 14 by separating the reservoir cap 76 from the reservoir 30. This permits the user to partially fill the reservoir 30 with a liquid or other fluid. The reservoir 30 is preferably made of a clear material to allow the user to view the amount of liquid in the reservoir 30. However, a transparent window may also be used. After partially filling the reservoir 30, the user re-attaches the on-board pump 14 by inserting the pump cylinder 40 into the reservoir 30 and securing the cap 76 to the reservoir 30. The user then can extend the pump piston 50 out of the pump cylinder 40 by holding both the pump handle 82 and the reservoir 30 and pulling the pump handle 82 away from the reservoir 30. Air will then enter the pump cylinder 40 by the top 54 of the pump piston 50. The user then pushes the pump piston 50 back into the pump cylinder 40, forcing air through the one-way valve cap 42 and into the reservoir 30. Repeatedly pumping air into the reservoir 30 will pressurize the liquid contained therein. When the pressure inside the reservoir 30 is substantially equal to the maximum pressure set by the pressure release valve 52, the air will no longer enter the reservoir 30 but will instead vent out of the pump cylinder 40 through the pressure release valve 52. Once the fluid or liquid inside the reservoir 30 is pressurized the user may release the pressurized liquid through a nozzle located in the head 18 of the oral cleaning device 10.

It may be further stated that the user can alter not only the force of the jetting liquid (or fluid) exiting the device 10 but also the duration such force is maintained. To alter the force of the jetting liquid (or fluid), the user may learn that for a specific water level inside the reservoir the user must pump air into the reservoir ten times (pressurizing the reservoir to a desired pressure). By reducing the number of times the user pumps air into the reservoir, the desired force of the liquid (or fluid) jetting out of the device 10 will decrease. In addition, the duration the force of the liquid (or fluid) jetting out of the device 10 is directly related to the level of liquid (or fluid) inside the reservoir for a specific pressure. As such, if the user reduces the liquid or (or fluid) level, but maintains the desired pressure inside the reservoir 30, the duration this desired force is maintained will increase. Similarly, if the user increases the liquid (or fluid) level, the duration will decrease. As such it may be preferred to have a fill line on the reservoir 30 that permits the user to fill the reservoir to a predetermined amount. This would provide the user with an optimum force of jetting liquid (or fluid) (when pressurized to the maximum pressure) for an optimum maximum duration. In addition, the secondary fill lines can relate to various head attachments, providing optimum settings for different cleaning tasks.

To transport the liquid (or fluid) from the reservoir 30 to the nozzle, a hose 84 is placed through the top aperture 34 of the reservoir 30 and into the reservoir 30. The hose 84 may contain a weight 86 on the end of the hose placed within the reservoir 30 in order to keep the end of the hose 84 near the bottom of the reservoir 30. The other end of the hose 84 is attached to a releasing/preventing mechanism 88 that when activated allows the pressurized liquid or fluid to travel through the neck 16 and out of the device 10.

The hose 84 is secured through an opening 92 (FIG. 2) in a top reservoir cap 90 that is secured to the top aperture 34 of the reservoir 30, along with a top reservoir gasket 91. The opening 92 is reinforced with a grommet 94 that places the hose 84 in fluid communication With an inlet 96 defined in the releasing/preventing mechanism 88. The releasing/ preventing mechanism 88 also includes a valve piston 102 that may be moved to an open position (allowing pressurized liquid or fluid to travel through) by a button 20. A valve spring 100 exerts a force onto the button 20 and the valve piston 102 that normally keeps the releasing/preventing mechanism 88 in a closed position (not allowing pressurized liquid or fluid to travel through). A valve pin 104 holds the button 20 in position with the valve piston 102 and valve spring 100. The releasing/preventing mechanism 88 and other components described for opening and closing the mechanism 88 is housed within a two piece housing 110. The front portion of the housing 110 includes an opening 112 to permit the button 20 to be pressed by a user. As mentioned, the releasing/preventing mechanism 88 is in a closed position unless the button 20 is pressed and held down by a user.

Figure 5:
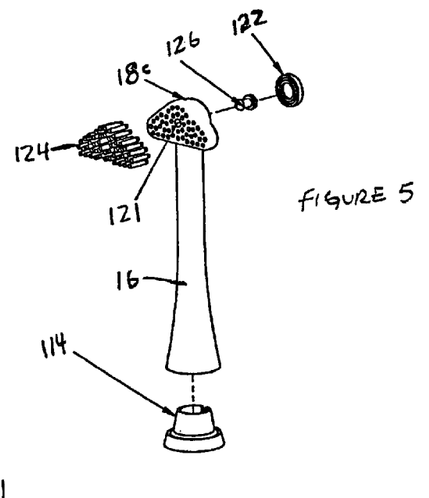
FIG. 5 is an exploded view of a head assembly illustrating a tongue brush.
Figure 6:
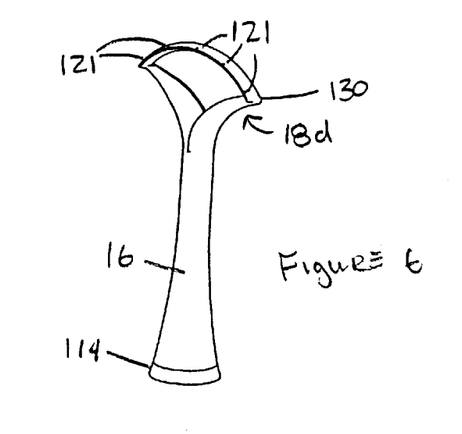
FIG. 6 is an perspective view of a head assembly illustrating a tongue scraper.

When opened the pressurized liquid or fluid travels through the releasing/preventing mechanism 88 and out an exit 106 defined thereon. The exit 106 of the releasing/ preventing mechanism 88 is in fluid communication with a channel 108 running through the neck 16. The neck 16 is secured to a neck base 114 that is removably attached to the exit 106. A neck o-ring 116 is preferably positioned between the neck base 114 and the two piece housing 110. The channel 108 travels through the neck 16 to at least one opening 121 in the head 18. Preferably a nozzle is positioned in the opening 121, in communication with the channel 108, and held in place by a nozzle cap 122. The nozzle may either be a long nozzle 120 for a head 18 that acts as a fluid jet (FIGS. 1–3) (more commonly referred to as a water jet when the fluid is water) or a short nozzle 126 for a head that also contains bristles 124 (FIGS. 4 and 5) or a head that is used for scraping (FIG. 6). A short nozzle 126 is preferably used when brushing or scraping because the nozzle does not interfere.

Figure 4:
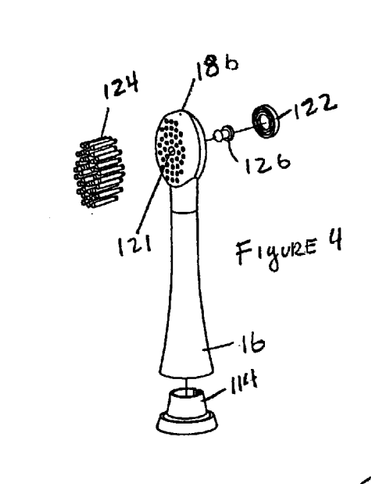
FIG. 4 is an exploded view of a head assembly that has a nozzle and bristles to brush teeth.

As shown in FIGS. 1–3, the head 18 of the device 10 contains a long nozzle 120. The long nozzle 120 provides the user with a cleaning device that is better suited to remove plaque and clean between teeth and gums (similar to flossing). In FIG. 4, the head 18b contains bristles 124 and a short nozzle 126. In addition the head 18b is shaped to provide the user with a brush better suited for their teeth, along with a nozzle to jet liquid or fluid for cleaning gums and teeth and rinsing. In FIG. 5, the head 18c contains a short nozzle 120 and a plurality of bristles 124 but contains a wider cross section than the head 18 in FIG. 4. This provides the user with a cleaning device that is better suited to clean the user's tongue. In FIG. 6, the head 18d does not contain bristles or a nozzle, the head 18d includes a projected edge 130 to scrape the user's tongue. The head 18d defined as a tongue scrape also includes at least one opening but preferably multiple openings 121 to spray liquid while the user is scrapping their tongue.

In addition, the fluid contained in the reservoir may be antiseptic or mouth wash for which the user can spray directly onto their tongue or in the mouth while brushing, scraping, rinsing or flossing.

As explained above, the present invention includes the ability to jet out a pressurized fluid, not only inclusive of a liquid but also a gas. For example, the user may simple pump air into and pressurize the air inside the reservoir. Once the reservoir contains a sufficient amount of pressurized air, the user may release it by pressing the button. While not as efficient as expelling pressurized liquid, in some instances the liquid, especially an antiseptic liquid, may be too sensitive for the user. Moreover, if pressurized gas such as air was the only intentional use of the device, the pump does not have to be removable, as the user can continuously refill the reservoir with air without removing the pump.

From the foregoing and as mentioned above, it will be observed that numerous variations and modifications may be effected without departing from the spirit and scope of the novel concept of the invention covering a self-contained device incorporating a reservoir, an on-board pump, and a nozzle into a single device with interchangeable heads to provide various oral cleaning actions. It is to be understood that no limitation with respect to the specific methods and apparatus illustrated herein is intended or inferred. It is intended to cover by the appended claims all such modifications as fall within the scope of the claims.

We claim:

1. An oral cleaning device comprising:
   a reservoir body having a lower aperture and a upper aperture;
   a manual operable removable pump attached to the reservoir body in communication with the lower aperture, the removable pump when removed from the reservoir body permits a user to fill the reservoir body with a liquid, and when the removable pump is attached to the reservoir body containing the liquid, the manual operation of said removable pump permits a user to increase pressure within the reservoir body such that the liquid contained in the reservoir body becomes pressurized liquid, the removable pump having a pressure release valve to vent excess pressure when the pressure within the reservoir reaches a predetermined pressure;
   a conduit means connecting the liquid under pressure with the upper aperture;
   a neck and head assembly attached to the reservoir body in communication with the upper aperture, the neck and head assembly having a channel in fluid communication with the conduit means and the neck and head assembly having an outlet aperture for expelling pressurized liquid contained in the reservoir body; and
   a mechanism in communication with the channel and the conduit means for controlling the flow of pressurized liquid from the reservoir body to the outlet aperture, thereby controlling the flow of pressurized liquid out of the device.

2. The oral cleaning device of claim 1, further comprising a nozzle positioned in the outlet aperture in the neck and head assembly and in fluid communication with the channel to jet pressurized liquid out of the device.

3. The oral cleaning device of claim 1, wherein the neck and head assembly is removable and interchangeable with another neck and head assembly having a different configuration to provide the user with a different cleaning implement.

4. The oral cleaning device of claim 1, wherein the neck and head assembly is defined as including a nozzle for irrigating gums, a brush with a nozzle for cleaning teeth, a brush with a nozzle for irrigating a tongue, or a tongue scraper with apertures for irrigating a tongue while scraping.

5. An oral cleaning device comprising:
   a reservoir body having a lower aperture and an upper aperture;
   a removable pump assembly attached to the reservoir body in communication with the lower aperture, the removable pump assembly when removed from the reservoir permits a user to fill the reservoir with the liquid, and when the removable pump assembly is attached to the reservoir body containing a liquid, the removable pump assembly permits a user to pressurize the liquid contained within the reservoir with air, wherein the removable pump assembly includes a pump cylinder with a one way valve to permit air to enter the reservoir, a pump piston slidably engaged within the pump cylinder, and a pressure release valve operably connected to the pump piston to permit air to vent when the pressure of the air contained within the reservoir reaches a predetermined pressure;
   a neck and head assembly attached to the reservoir body in communication with the upper aperture, the neck and head assembly having a channel in fluid communication with the reservoir and the neck and head assembly having an outlet aperture for expelling pressurized liquid contained within the reservoir; and
   a mechanism disposed between the channel and the reservoir for controlling the flow of pressurized liquid from the reservoir to the channel, thereby controlling the flow of pressurized liquid out of the device.

6. An oral cleaning device having a body, a neck extending from the body and a head attached to the neck, the oral cleaning device further comprising:
   a reservoir defined by the body of said oral cleaning device for holding a liquid;
   a means for filling the reservoir with a liquid;
   a manual means to pressurize the liquid contained in the reservoir with air, said pressurizing means attached to and movable relative to the body, said pressurizing means includes a pressure release valve to vent excess air when a pressure within the reservoir reaches a pre-defined optimum pressure; and
   a channel defined in the neck and having one end in fluid communication with the reservoir and having another end attached to an opening defined in the head of the oral cleaning device, conduit means connecting the pressurized liquid with said channel and means for controlling the flow of pressurized liquid through said conduit means such that pressurized liquid traveling through the channel may exit the oral cleaning device at the opening.

7. The oral cleaning device of claim 6 in which the means for controlling the flow of the pressurized liquid from the reservoir to the channel includes a valve assembly.

8. The oral cleaning device of claim 7, wherein the neck and head is removably connected to the oral cleaning device.

9. The oral cleaning device of claim 8, wherein the head includes a nozzle in fluid communication with the channel to jet the pressurized liquid out of the device.

10. The oral cleaning device of claim 9, wherein the head includes bristles positioned about the nozzle and includes a predetermined shape defined for a tongue brush, or a tooth brush.

11. The oral cleaning device of claim 8, wherein the head includes a projecting edge that define a plurality of openings in the projecting edge.

12. The oral cleaning device of claim 6, wherein the pressurizing means includes:
   a pump cylinder having a one-way valve secured on an end of the pump cylinder and said end of the pump cylinder is in fluid communication with the reservoir, the one-way valve only permits air to enter the reservoir; and a pump piston slidably engaged within the pump cylinder, the pump piston having a head that includes a means to permit air to enter the pump cylinder when the pump piston is moved outwardly relative to said end of the pump cylinder, and the means to force said air in the pump cylinder to enter the reservoir through the one-way valve when the pump piston is moved inwardly relative to said end of the pump cylinder, and wherein the pressure release valve is attached to the head of the pump piston.

13. The oral cleaning device of claim 6, wherein the controlling means is defined by a valve control mechanism attached between the reservoir and the neck, the valve control mechanism includes a button that when pressed opens a valve to allow the pressurized liquid in the reservoir to travel to the channel and when the button is released said valve closes to prevent the pressurized liquid in the reservoir from entering the channel.

14. An oral cleaning device comprising:
a reservoir to hold a liquid, the reservoir having at least first and second apertures and a bottom portion;
a manually operated pump means in communication with the first aperture defined by the reservoir for pumping air into the reservoir and said pump means capable of continuous operation to increase a pressure within the reservoir such that the liquid contained within said reservoir is pressurized by air;
the first aperture having a removable cap attached thereto, wherein when said removable cap is removed the reservoir may be filled with a liquid and when said removable cap is attached the reservoir is substantially sealed to prevent leaking;
a neck and head assembly having a channel in communication with the second aperture of the reservoir, and having a nozzle in fluid communication with the channel;
a tube positioned within the reservoir and having a first end and a second end, the second end in communication with the channel via the second aperture and the first end being opened to the reservoir to directly convey liquid from the reservoir into the tube and being in proximity to the bottom portion such that the tube allows for the substantially complete evacuation of the liquid in the reservoir when said liquid contained in said reservoir is pressurized, the tube and the channel forming a conduit means to permit pressurized liquid within the reservoir to jet out of the nozzle; and
a fluid control mechanism in communication with the conduit means includes a valve that when closed prevents the pressurized liquid contained in the reservoir from jetting out of the nozzle and includes a release means that opens the valve to permit the pressurized liquid contained in the reservoir to jet out of the nozzle,
whereby when the reservoir contains a pressurized liquid, the pressurized liquid is capable of being released through the nozzle contained in the neck and head assembly, when the valve is opened.

15. The oral cleaning device of claim 14, wherein the neck and head assembly is defined to clean a first portion of the user's mouth and is removable and interchangeable with a second neck and head assembly defined to clean a second portion of the user's mouth different than the first portion.

16. The oral cleaning device of claim 15, wherein the second neck and head assembly includes bristles positioned about the nozzle.

17. The oral cleaning device of claim 15, wherein the second neck and head assembly includes a projected edge with at least one opening to permit the liquid to expel from the head.

18. The oral cleaning device of claim 14, wherein the pump means includes:
a pump cylinder having a one-way valve secured on an end of the pump cylinder and said end of the pump cylinder is in fluid communication with the reservoir, the one-way valve permits air to enter the reservoir and prevents fluids from exiting the reservoir;
a pump piston slidably engaged within the pump cylinder, the pump piston having a head that when the pump piston is moved outwardly relative to said end of the pump cylinder, air enters the pump cylinder and when moved inwardly relative to said end of the pump cylinder, air is forced into the reservoir through the one-way valve; and
a pressure release valve attached to the pump piston, the pressure release valve permits the air in the pump cylinder to vent when the pressure of the air in the reservoir reaches a pre-defined pressure.

19. The oral cleaning device of claim 14, wherein the manually operated pump is removably attached to the reservoir in communication with the first aperture and the manually operated pump when removed allows the reservoir to be filled with a liquid through the first aperture and the manually operated pump is movable relative to the reservoir such that when attached, the manually operated pump allows a liquid contained in the reservoir to be pressurized with air.

20. A hand-held device comprising:
a body that a user may grasp during use of said device, the body containing a reservoir for holding a liquid;
a means for filling the reservoir with the liquid;
a mechanical means to increase a pressure exerted on the liquid contained in the reservoir to create a pressurized liquid, said mechanical pressurizing means attached to and movable relative to the body;
a control mechanism in communication with an aperture defined by the reservoir for selectively controlling the flow of pressurized liquid out of the reservoir;
a first attachment head removably attached to the control mechanism, the head having an opening for expelling the pressurized liquid from the device when the control mechanism is in an open position, the first attachment head is selectively replaceable with a second attachment head having a different configuration than the first attachment head; and
a means to release pressure while the liquid contained within the reservoir is being pressurized with the mechanical pressurizing means and when the pressure in the reservoir reaches a pre-defined pressure, the pressure releasing means being attached to the mechanical pressurizing means.

21. A portable oral cleaning device for dispensing a high velocity, high pressure, low viscous fluid, the device having a hand-held body, a neck extending from the body and a head attached to the neck, the oral cleaning device further comprising:
a reservoir defined by the body for holding a low viscous liquid;
a filling aperture disposed in the body for filling the reservoir with a low viscous liquid;
a pumping mechanism movably attached to the body for increasing pressure in the reservoir and wherein continued operation of said pumping mechanism positively pressurizes the low viscous liquid contained in said reservoir, the pumping mechanism including a pressure release valve to vent excess pressure when the pressure in the reservoir reaches a pre-determined pressure;

a channel defined in the neck and having one end in fluid communication with the reservoir and having another end in fluid communication with an outlet aperture defined in the head of the device;

a valve mechanism disposed between the channel and the reservoir, and a button for selectively placing the valve mechanism in an open and closed position, wherein when the valve mechanism is in a closed position, the low viscous fluid contained in said reservoir is able to become highly pressurized by repeated operation of said pumping mechanism; and a nozzle positioned in said outlet aperture for accelerating a velocity of the low viscous fluid being dispensed from the oral cleaning device, whereby when the reservoir contains the low viscous fluid and when the valve mechanism is in the closed position the low viscous fluid becomes highly pressurized from the repeated operation of the pumping mechanism such that thereafter the valve mechanism being placed in the open position permits the highly pressurized, low viscous fluid to flow into the nozzle whereupon the velocity of the highly pressurized, low viscous fluid increases such that the device dispenses a high velocity, highly pressurized, low viscous fluid.

22. The device of claim 21, wherein the pumping mechanism is removably attached to the filling aperture.

23. The device of claim 22, wherein the pumping mechanism is defined as having:

an elongated pump cylinder having one end disposed within the reservoir and another end removably secured about the filling aperture, and a pump piston slidably engaged within the pump cylinder and having a top portion and a bottom portion, said bottom portion being secured to a pump handle, the top portion including a seal sized to seal against an inner surface defined by the pump cylinder, the top portion further including grooves which work in concert with the seal to permit air to enter the pump cylinder when the pump piston is manually moved outwardly relative to the pump cylinder via the pump handle and pushes the air in said pump cylinder into the reservoir when the pump piston is manually moved inwardly relative to the pump cylinder.

24. The device of claim 23 further comprising:

a tube positioned within the reservoir and having a first end and a second end, the first end being positioned in proximity to a bottom defined by the reservoir and the second end in fluid communication with the channel, wherein the first end being in proximity to the bottom of the reservoir permits substantially complete evacuation of the liquid in the reservoir when the reservoir includes a high pressure low viscous liquid pressurized to a predetermined pressure.

25. An oral cleaning device comprising:

a body which a user may grasp during use, the body having a reservoir that has first and second apertures and is sufficiently hollow;

a pump means removably attached to the reservoir in communication with the first aperture, the pump means when removed from the reservoir permits a user to fill the reservoir with a liquid via the first aperture and when the pump means is attached to the reservoir, the pump means is operated to pump a gas into the reservoir such that continually operating said pump means increases the pressure within the body to create a positively pressurized liquid within the reservoir;

a tube contained within the reservoir and attached to the second aperture and having one end opened to the reservoir to directly convey fluid from the reservoir into the tube and in proximity to a bottom defined by the reservoir such that substantially all of the pressurized liquid contained in the reservoir is evacuated when the pressurized liquid is pressurized to a predetermined pressure;

a neck and head assembly attached to the body and having a channel in fluid communication with the tube to define a conduit means for delivering pressurized fluid from the reservoir to an outlet aperture in the neck and head assembly and;

a valve mechanism attached to the conduit means which when placed in an open position permits positively pressurized liquid contained within the body to flow out of the outlet aperture in the neck and head assembly.

26. The oral cleaning device of claim 25, wherein the pump means includes a cylinder and a piston slidably engaged within the cylinder, the cylinder having a one way valve permitting air to enter the reservoir and the piston having a pressure release valve permitting air to vent when the pressure within the body reaches a predetermined pressure, the pump cylinder and pump piston work in concert to force air into the body and increase the pressure exerted onto the liquid contained within the reservoir until the pressure reaches the predetermined pressure at which point excess air is vented through the pressure release valve.

27. The oral cleaning device of claim 26, wherein the neck and head assembly is defined to clean a first portion of the user's mouth and is removable and interchangeable with a second neck and head assembly defined to clean a second portion of the user's mouth different than the first portion.

28. The oral cleaning device of claim 27, wherein the second neck and head assembly includes bristles positioned about a nozzle positioned in the aperture of the head portion.

29. The oral cleaning device of claim 27, wherein the second neck and head assembly includes a projected edge with at least one opening to permit the liquid to expel from the head.

30. An oral cleaning device having a body for a user to grasp, the device further comprising:

a refillable reservoir contained within said body for holding a first fluid within said reservoir;

a pump means being attached to the body in communication with a first aperture defined by the reservoir the reservoir to pump a second fluid into the reservoir in order to increase a pressure exerted onto the first fluid contained within the reservoir, wherein continued operation of said pump means increase said pressure exerted onto the first fluid contained within said reservoir to create a pressurized first fluid;

a tube positioned within the reservoir and having a one end secured to a second aperture defined by the reservoir and another end opened to the reservoir to directly convey fluid from the reservoir into the tube, said other end also positioned in proximity to a bottom defined by the reservoir, such that the pressurized first fluid contained within the reservoir is substantially evacuated during use when the pressurized first fluid is pressurized to a predetermined pressure;

a neck and head assembly attached to the body in communication with the second aperture, the neck having a channel in communication with the tube and the head having an outlet for discharging the pressurized first fluid contained within the reservoir; and a mechanism disposed between the channel and the second aperture for controlling the flow of the pressurized first fluid contained within the reservoir to the channel, thereby controlling the discharge of pressurized first fluid out of the device.

31. The oral cleaning device of claim 30, wherein the pump means is removably attached to the body in communication with the first aperture defined by the reservoir, when the pump means is removed said first aperture permits the reservoir to be filled with a liquid.

32. The oral cleaning device of claim 31, wherein the pump means is further defined as including a pump cylinder and a pump piston working in concert to force the second fluid into the reservoir through a one-way valve positioned between said pump cylinder and said pump piston and said pump piston includes a pressure release valve to vent excess second fluid when the pressure of the second fluid within the reservoir reaches the predetermined pressure.

33. The oral cleaning device of claim 32, wherein the pump cylinder is secured within the reservoir about the first aperture and the pump piston is secured to a handle that a user may grasp and when said pump piston is extended away from said pump cylinder the pump cylinder fills with the second fluid and when said pump piston is pushed toward the pump cylinder, the second fluid is urged into the reservoir to pressurize the first fluid.

* * * * *